(12) United States Patent
Vanderslice et al.

(10) Patent No.: US 9,546,943 B1
(45) Date of Patent: Jan. 17, 2017

(54) SYSTEM AND METHOD FOR INVESTIGATING CHANGE IN OPTICAL PROPERTIES OF A POROUS EFFECTIVE SUBSTRATE SURFACE AS A FUNCTION OF A SEQUENCE OF SOLVENT PARTIAL PRESSURES AT ATMOSPHERIC PRESSURE

(71) Applicant: J.A. WOOLLAM CO., INC., Lincoln, NE (US)

(72) Inventors: Jeremy A. Vanderslice, Lincoln, NE (US); Christopher A. Goeden, Lincoln, NE (US); Martin M. Liphardt, Lincoln, NE (US)

(73) Assignee: J.A. WOOLLAM CO., INC, Lincoln, NE (US)

( * ) Notice: Subject to any disclaimer, the term of this patent is extended or adjusted under 35 U.S.C. 154(b) by 0 days.

(21) Appl. No.: 14/999,015

(22) Filed: Mar. 18, 2016

Related U.S. Application Data

(60) Provisional application No. 62/177,782, filed on Mar. 21, 2015.

(51) Int. Cl.
  *G01N 15/00*  (2006.01)
  *G01N 15/08*  (2006.01)
  *G01N 21/21*  (2006.01)

(52) U.S. Cl.
  CPC ......... *G01N 15/0826* (2013.01); *G01N 21/211* (2013.01)

(58) Field of Classification Search
  CPC ................ G01N 15/088; G01N 21/211; G01N 2015/0846; G01J 1/02; G01J 1/0252
  See application file for complete search history.

(56) References Cited

U.S. PATENT DOCUMENTS

| | | | |
|---|---|---|---|
| 6,319,736 B1 | 11/2001 | Baklanov et al. | |
| 6,435,008 B2 | 8/2002 | Baklanov et al. | |
| 6,662,631 B2 | 12/2003 | Baklanov et al. | |
| 7,042,570 B2 * | 5/2006 | Sailor | G01N 21/55 356/445 |
| 7,426,030 B1 * | 9/2008 | Liphardt | G01J 1/02 356/367 |
| 7,458,251 B2 * | 12/2008 | Baklanov | G01N 15/082 427/8 |
| 7,534,631 B2 * | 5/2009 | Griffiths | C30B 25/14 438/16 |
| 7,817,266 B2 | 10/2010 | Pfeiffer et al. | |
| 7,906,174 B1 * | 3/2011 | Wu | C23C 16/401 427/248.1 |
| 8,130,357 B2 * | 3/2012 | Kim | G02F 1/136213 200/600 |
| 8,130,375 B1 | 3/2012 | Pfeiffer et al. | |

(Continued)

OTHER PUBLICATIONS

"Porosity and Mechanical Properties of Mesoporous Thin Films Assessed by Environmental Ellipsometric Porosimetry"; Boissiere et al., Langmuir 2005, 21, 12362-12371.

(Continued)

*Primary Examiner* — Sang Nguyen
(74) *Attorney, Agent, or Firm* — James D. Welch (57) ABSTRACT

A system for and method of investigating changes in optical properties of a porous effective substrate surface related to, for instance, effective surface depth and refractive index, pore size, pore volume and pore size distribution at atmospheric pressure.

13 Claims, 4 Drawing Sheets

(56) References Cited

U.S. PATENT DOCUMENTS

| | | | |
|---|---|---|---|
| 8,248,606 B1 * | 8/2012 | Liphardt | G01N 21/211 |
| | | | 356/369 |
| 8,493,565 B1 | 7/2013 | Pfeiffer et al. | |
| 8,531,665 B1 | 9/2013 | Pfeiffer et al. | |
| 9,007,593 B2 * | 4/2015 | Sailor | G01N 21/171 |
| | | | 356/326 |
| 2009/0019921 A1 * | 1/2009 | Simon | G01N 15/088 |
| | | | 73/38 |

OTHER PUBLICATIONS

"Carbon Dioxide Mediated Synthesis of Mesoporous Silica Films: Tuning Properties Using Pressure"; Li and Vogt, Chem. Matter, XXX, xxx, Published on web Apr. 18, 2008.

"Characterization of Ordered Mesoporous Silica Films Using Small-Angle Neutron Scattering and X-Ray Porosimetry"; Vogt et al., Chem Matter 2005, 17, 1398-1408.

* cited by examiner

FIG. 1a

PRIOR ART

SYSTEM AND METHOD FOR INVESTIGATING CHANGE IN OPTICAL PROPERTIES OF A POROUS EFFECTIVE SUBSTRATE SURFACE AS A FUNCTION OF A SEQUENCE OF SOLVENT PARTIAL PRESSURES AT ATMOSPHERIC PRESSURE

This Application Claims benefit of Provisional Application Ser. No. 62/177,782 filed Mar. 21, 2015.

TECHNICAL FIELD

The present invention relates to systems and methods for investigating substrates, and more particularly to a system for, and method of investigating changes in optical properties of a porous effective substrate surface related to, for instance, effective surface depth and refractive index, pore size, pore volume and pore size distribution at atmospheric pressure.

BACKGROUND

It is known to deposit thin films that contain known analytes onto a substrate from an analyte containing liquid. For instance, Patents to Pfeiffer et al., U.S. Pat. Nos. 8,531,665, 8,493,565, 8,130,375 and 7,817,266 describe Small Cells into which analyte containing fluid is caused to flow, to the end that analyte present in said fluid deposits onto a substrate. Provision for an ellipsometer beam to be directed onto said thin analyte containing film is also present, and during use a polarized beam of electromagnetic radiation is caused to interact with the thin film on said substrate and then enter a detector.

It is also known to characterize effective surfaces of substrates comprising pores, by transiently causing solvents to permeate thereinto long enough to allow ellipsometric investigation thereof, for a sequence of solvent values. Known relevant references are: Patents to Baklanov et al. U.S. Pat. Nos. 6,435,008; 6,319,736, and 6,662,631; and papers by Boissire et al, titled "Porosity and Mechanical Properties of Mesoporous Thin Films Assessed by Environmental Ellipsometric Porosity", Langmuir 2005, 21, 12362-12371; by Xinxin and Vogt Titled "Carbon Dioxide Mediated Synthesis of Mesoporous Silica Films: Tuning Properties using Pressure", Chem. Mater. Amer. Chem. Soc., Web Apr. 18, 2008. and by Vogt et al., titled "Characterization of Ordered Mesoporous Silica Films Using Small-Angle Neutron scattering and X-ray Porosimetry", Chem. Mater., 17, 1398-1408. Note that said references do not describe use at atmospheric pressure.

In further disclosure, Applicants know of no prior art systems which rely on direct measurement of partial pressure in an open (to the ambient) cell. Known prior art systems use closed cells and apply a feedback system to control a solvent flow rate into said open cell to set a desired partial pressure. In addition, known partial pressure monitors are suitable only when water is the solvent involved. As disclosed in the following in this Specification, the present invention applies open chambers in which partial pressures are developed. Further, as disclosed in the following, the present invention is not limited to using only water as a solvent.

What is, to the inventor's knowledge, not previously known is a system and method for investigating changes in optical properties of a porous effective substrate surface related to, for instance, effective surface depth and refractive index, pore size, pore volume and pore size distribution at atmospheric pressure, said system enabling the flowing of a gas that contains at least one solvent therein which is flowed over said substrate surface at a monitored temperature, over a sequence of different known solvent partial pressures. Such a system and method are disclosed herein.

DISCLOSURE OF THE INVENTION

The present invention is a system for investigating changes in optical properties of a porous effective substrate, that comprises a surface, related to, for instance, effective surface depth and refractive index, pore size, pore volume and pore size distribution at atmospheric pressure, said system enabling flowing of a gas that contains at least one solvent therein which is flowed over said substrate surface at a monitored temperature, over a sequence of different known solvent partial pressures.

The present invention system comprises:

a) at least one source of a flow of at least one solvent and a solvent mass flow causing controller;

b) a source of a flow of gas and a gas mass flow causing controller;

c) an atomizing nozzle for receiving both a flow of at least one solvent and of a flow of gas, and expelling a mixture of said at least one solvent in said gas over said substrate at a sequence of solvent partial pressures;

d) an open chamber comprising said substrate that comprises a surface, and a temperature monitoring sensor; said system not comprising a partial pressure sensor feedback loop to control partial pressure values in said open chamber, but rather, partial pressure values in said open chamber are set entirely by direct control of solvent flow rate of said at least one solvent in view of a measured temperature;

such that in use said temperature sensor provides a measurement of temperature, and said atomizing nozzle receives both a flow of gas and at least one solvent from said gas and solvent mass flow causing controllers associated with said source of a flow of gas, and of said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures;

said partial pressure of said solvent being determined from said measured temperature and solvent flow rate.

In use said temperature sensor provides a measurement of temperature, and said atomizing nozzle receives both a flow of gas and at least one solvent from said flow causing controllers associated with said source of a flow of gas, and of said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures.

Said system can further comprises an ellipsometer system comprising a polarization state generator oriented so as to direct a polarized beam of electromagnetic radiation at said surface of said substrate, and a polarization state detector oriented to detect said beam of electromagnetic radiation after it interacts with said surface of said substrate, and produce substrate surface characterizing data.

The system can be present in open atmosphere wherein the static pressure in said open chamber is neither greater than or less than that of the open atmosphere.

Said system can be present in a common ambient environment with other than atmosphere components in their common ratios, and wherein the static pressure in said open chamber is neither greater than or less than that of the common ambient atmosphere, which common ambient atmosphere is substantially equal to prevailing atmospheric pressure.

Said system can provide that a thin film is present on said substrate surface.

Said method can involve using a solvent which is water, or is other than water. It is emphasized that in the later case, Applicant knows of no partial pressure sensor that could be applied in prior art closed cell systems.

A present invention method for investigating changes in optical properties of a substrate surface, comprising the steps of:

A) providing a system for investigating changes in optical properties of a porous effective substrate, that comprises a surface, related to, for instance, effective surface depth and refractive index, pore size, pore volume and pore size distribution at atmospheric pressure, said system enabling flowing of a gas that contains at least one solvent therein which is flowed over said substrate surface at a monitored temperature, over a sequence of different known solvent partial pressures, said system comprising:

a) at least one source of a flow of at least one solvent and a solvent mass flow causing controller;

b) a source of a flow of gas and a gas mass flow causing controller;

c) an atomizing nozzle for receiving both a flow of at least one solvent and of a flow of gas, and expelling a mixture of said at least one solvent in said gas over said substrate at a sequence of solvent partial pressures;

d) an open chamber comprising said substrate that comprises a surface, and a temperature monitoring sensor;

Said system, however, does not comprise a partial pressure sensor feedback loop to control partial pressure values in said open chamber, but rather, partial pressure values in said open chamber are set entirely by direct control of solvent flow rate of said at least one solvent in view of a measured temperature.

In use said temperature sensor provides a measurement of temperature, and said atomizing nozzle receives both a flow of gas and at least one solvent from said gas and solvent mass flow causing controllers associated with said source of a flow of gas, and of said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures;

said partial pressure of said solvent being determined from said measured temperature and solvent flow rate.

Said system further comprises:

e) providing an ellipsometer system comprising a polarization state generator oriented so as to direct a polarized beam of electromagnetic radiation at said surface of said substrate, and a polarization state detector oriented to detect said beam of electromagnetic radiation after it interacts with said surface of said substrate, and produce substrate surface characterizing data.

In use said atomizing nozzle receives both a flow of gas and at least one solvent from said source of a flow of gas and from said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures.

Also in use, said ellipsometer polarization state generator directs a polarized beam of electromagnetic radiation at said surface of said substrate, and a polarization state detector detects said beam of electromagnetic radiation after it interacts with said surface of said substrate, and produce substrate surface characterizing data.

The method continues with:

B) causing said atomizing nozzle to receive both a flow of gas and at least one solvent from said source of a flow of gas and from said at least one source of a flow of at least one solvent, respectively, and in response expel a mixture of said at least one solvent in said gas, so as to effect a sequence of solvent partial pressures, which mixture is caused to pass over said substrate surface in said open chamber in a manner such that said solvent transiently permeates said substrate surface long enough for data to be acquired therefrom by causing said ellipsometer polarization state generator to direct a polarized beam of electromagnetic radiation at said surface of said substrate, and said polarization state detector to detect said beam of electromagnetic radiation after it interacts with said surface of said substrate, and produce substrate effective surface characterizing data for at least some of said sequence of solvent partial pressures;

C) for a temperature provided by said temperature monitoring sensor of said open chamber, analyzing and/or displaying at least some of the effective substrate surface characterizing data.

Said method can provide that at least two substrate surface associated parameters are evaluated as a function of solvent partial pressure of said at least one solvent at a known temperature, by analysis of produced substrate effective surface characterizing data, said at least two parameters being selected from the group consisting of:
  substrate effective surface thickness;
  substrate effective surface refractive index;
  substrate surface pore size;
  substrate surface pore volume; and
  substrate surface pore size distribution.

The partial pressure of said solvent is determined from said measured temperature and solvent flow rate. When water is the solvent, published tables are available to relate solvent flow rate, and measured temperature, to partial pressure. Where water is not the solvent, the present invention method further comprises compiling an appropriate table.

Said method can involve a thin film being present on said substrate surface.

Said method can involve using a solvent which is water, or is other than water.

Said method can further comprise developing a Look-up table that comprises, for the solvent utilized, correlation between solvent flow rate and temperature, and partial pressure and using said table to determine specific partial pressures, given a solvent flow rate caused by said solvent flow causing controller, and measured temperature.

The present invention will be better understood by references to the Detailed Description Section of this Specification, in conjunction with the Drawings.

DETAILED DESCRIPTION

Figure 1A:
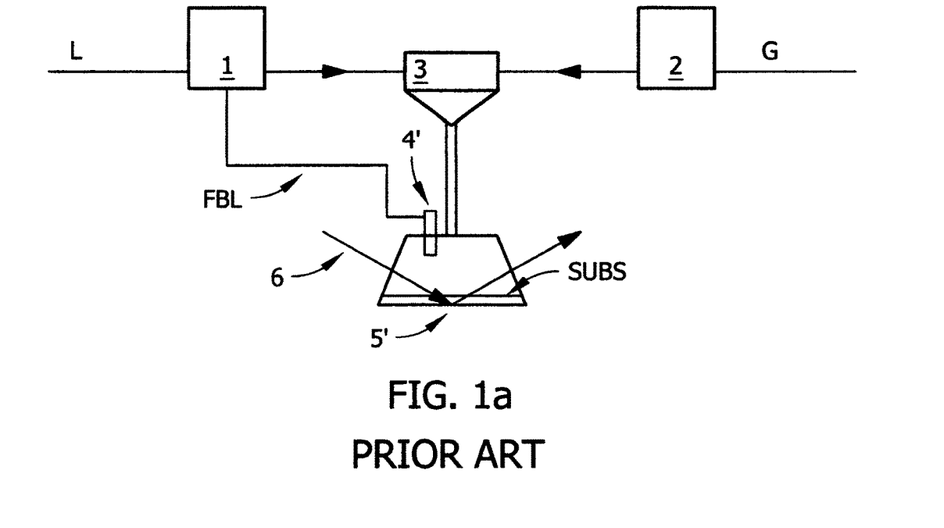
FIG. 1a shows the basic system of prior art systems.

Turning now to the Drawings, FIG. 1a shows a Prior Art System. Much as in the Present Invention system there is an Environment Chamber (5'), (typically not open to the environment), said Environmental Chamber (5') comprising a substrate (SUB) therewithin. Said Environmental Chamber (5') is present in conjunction with a Solvent Mass Flow Controller (1), (ie. a source of a flow of at least one solvent (L)), a Gas Mass Flow Controller (2), (ie. a source of a flow of gas (G)), and an Atomizing Nozzle (3) with access to said Environmental Chamber (5').

Figure 1B:
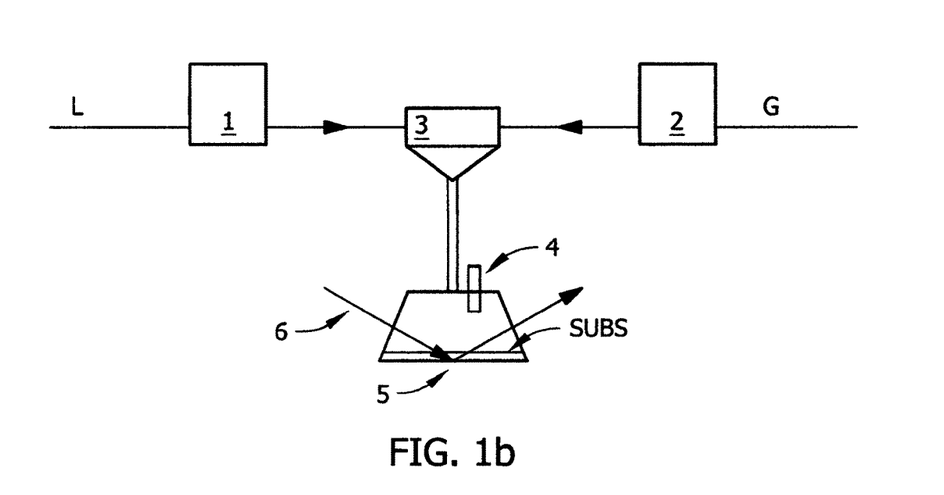
FIG. 1b shows the basic system of the present invention.

FIG. 1b shows an Open Environment Chamber (5) of the present invention system, comprising a substrate (SUB) therewithin, in conjunction with a Solvent Mass Flow Controller (1), (ie. a source of a flow of at least one solvent), a Gas Mass Flow Controller (2), (ie. a source of a flow of gas (G)), an Atomizing Nozzle (3), and an Open Atmosphere Chamber (5) comprising said substrate (SUB) and a Temperature Monitoring Sensor (4). It is pointed out that the Open Atmosphere Environment Chamber (5) is unique in view of all known Prior Art in that it does not require a Humidity (vapor) Sensor feedback loop for use in controlling a Partial Pressure in the Open Atmosphere Chamber (5). There is a Temperature Sensor (4) present, however, which is used to monitor Temperature in the Open Atmosphere Environmental Chamber (5), not control it. Further, the Atomizing Nozzle (3) can be used to vaporize any Solvent, (ie. there is no limitation on what Solvent is used but commonly used Solvents to date by the Inventors have been Water, Toluene and Methanol).

Figure 4:
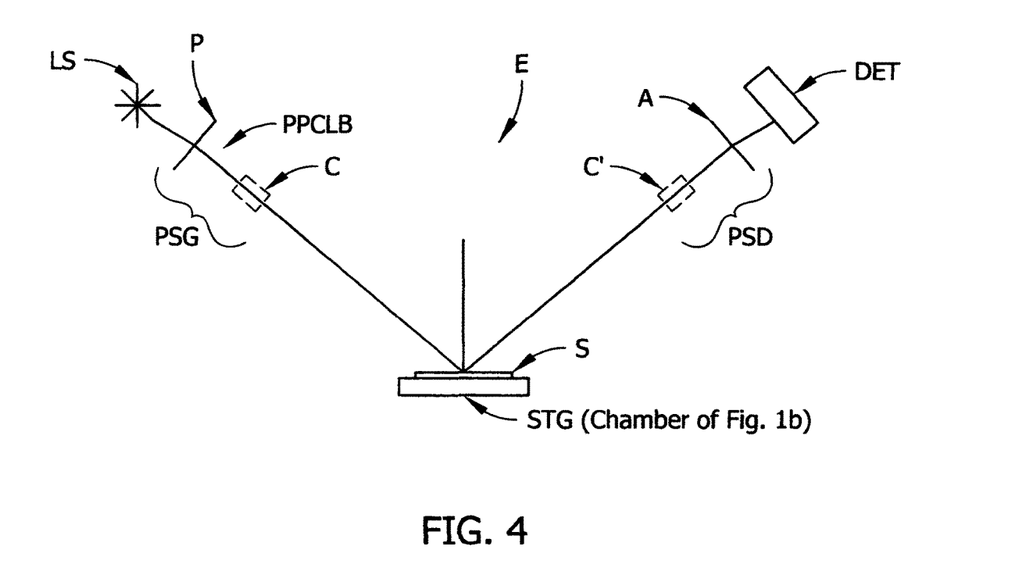
FIG. 4 shows a more generally an Ellipsometer System (E).

Also shown in both FIGS. 1a and 1b is an Ellipsometer System polarized beam (6) of electromagnetic radiation oriented to progress toward said surface of said substrate (SUB) and then exit said Open Atmosphere Environmental Chamber (5) and proceed toward a Detector thereof, (see FIG. 4 (DET)).

Note, there is a major difference between the FIG. 1a prior art and the present invention as is shown in FIG. 1b, in that the FIG. 1a prior art system comprises a Partial Pressure Sensor (4') which is part of Feedback Loop (FBL) that provides the Solvent Mass Flow Controller (1) a signal based on measured properties in said Environmental Chamber (5'). Said Solvent Mass Flow Controller (1) uses that Feedback Loop (FBL) provided Signal to control the rate at which Solvent (L) is provided therethough. It is also noted that known systems for monitoring partial pressure (4') and providing a feedback signal (FBL) work only for the case wherein water is the liquid. The present invention is not so limited, and any liquid can be used.

Figure 2:
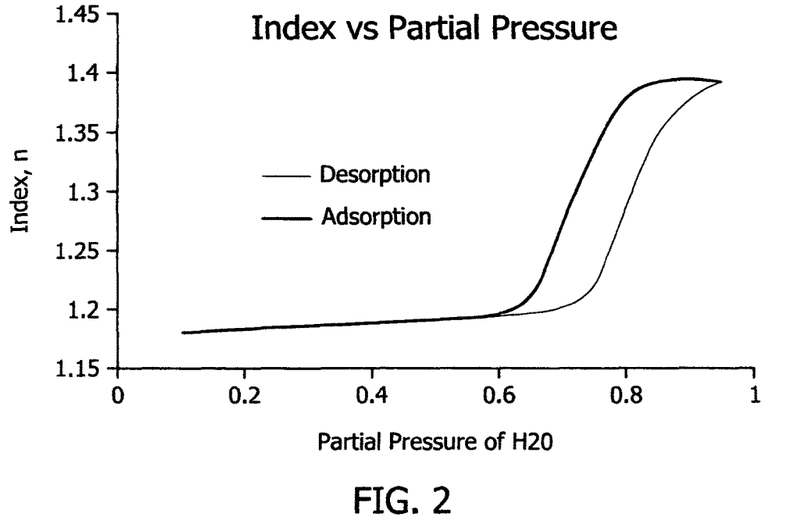
FIG. 2 demonstrates change of Index of Refraction vs. Partial Pressure of H2O for a sample investigated by the method of the present invention.
Figure 3:
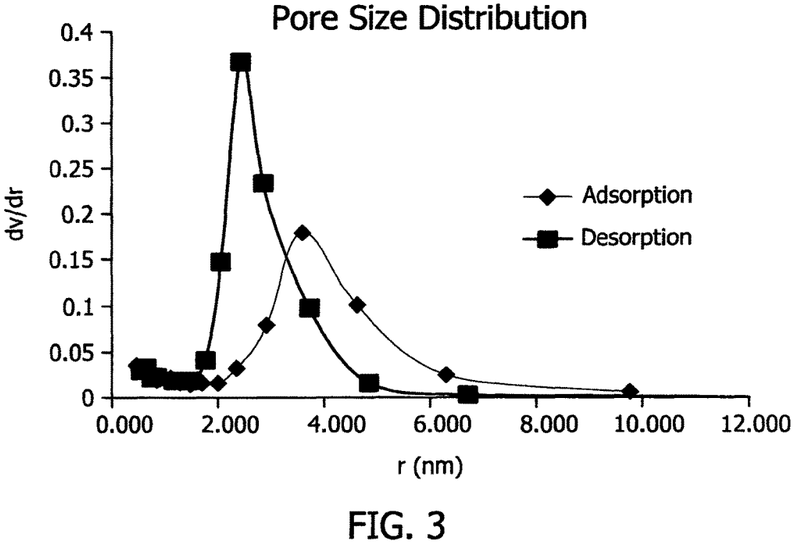
FIG. 3 demonstrates Pore Size Distribution vs. Partial Pressure of H2O for a sample investigated by the method of the present invention.

FIG. 4 shows a more generally an Ellipsometer System (E) which comprises a Source of Electromagnetic Radiation (LS), a Polarization State Generator (PSG) which comprises a Polarizer (P) and optional Compensator (C), oriented so as to direct a polarized beam of electromagnetic radiation (PPCLS) at said Surface of a Sample (S) on said Stage (STG), which can be present in said Open Atmosphere Environmental Chamber (5) of FIG. 1b and form the Substrate (SUBS). Note that in FIG. 1b the terminology "Open" indicates that a mixture of Gas and Solvent exiting said Atomizing Nozzle (3) freely enters into the Open Atmosphere Environmental Chamber (5) from above as shown, and approaches the Substrate (SUBS). Further shown is a Polarization State Detector (PSD) oriented to detect said beam of electromagnetic radiation after it interacts (eg. reflects from), with said surface of said Substrate (SUBS), enters a Detector (DET) which produces Substrate Surface Characterizing Data. Analysis of such Characterizing Data according to the Process Flow Overview outlined in FIG. 5, allows arriving at results such as the Index of Refraction and Pore Size shown in FIGS. 2 and 3 respectively.

Figure 5:
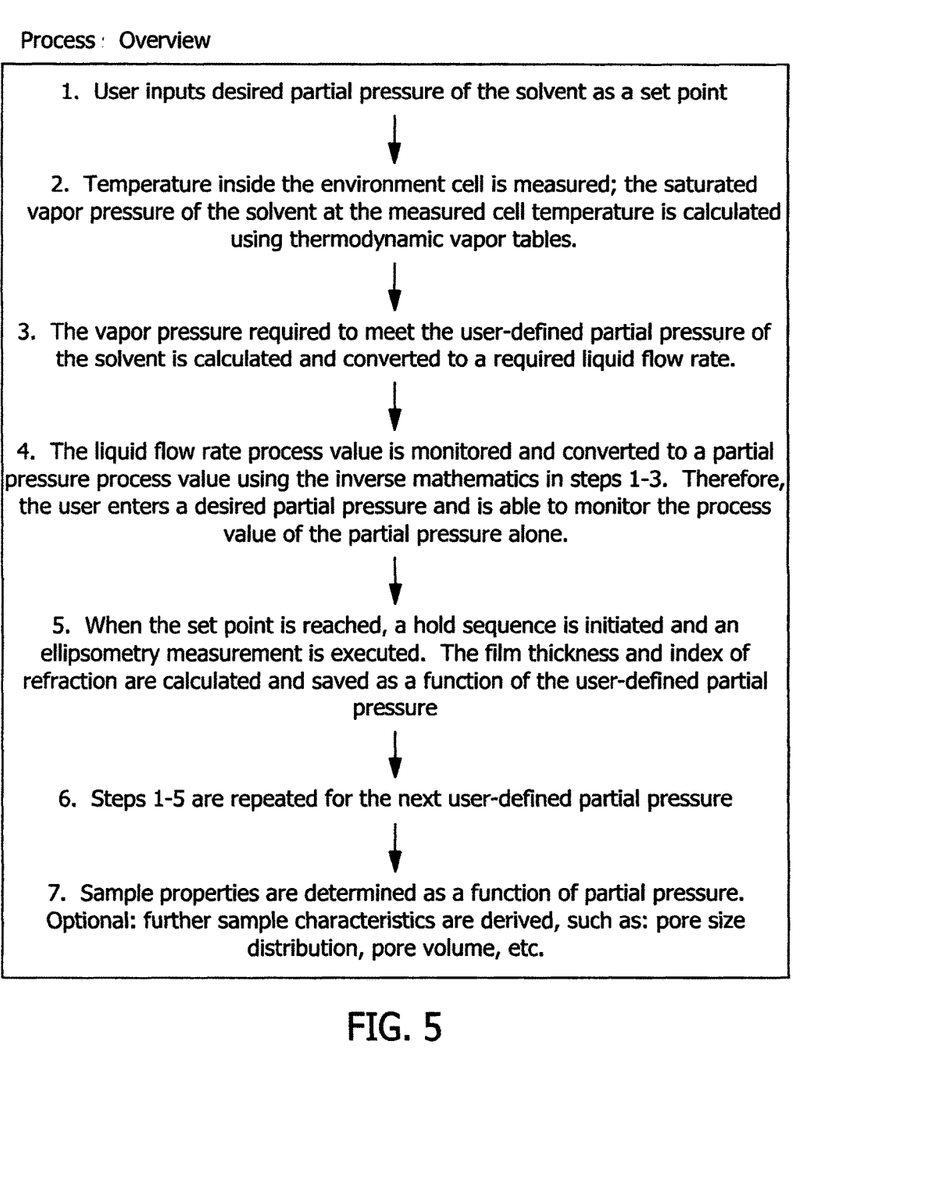
FIG. 5 is a listing of an Overview of the Method of Use Process of the present invention method.

FIG. 5 shows a flow chart of the present invention Method, providing that in use a controlled amount of solvent is vaporized by said Nozzle (3) to provide an intended Solvent Partial Pressure in a flow of Gas at the Open Chamber (5). This is directly presented to the Substrate Surface (SUBS) so that it transiently permeates thereinto long enough to allow Characterizing Ellipsometric Data to be acquired. The methodology requires this be done for a sequence of Partial Solvent Pressure. It is further noted that practice of the present invention involves measuring a temperature and setting a solvent flow rate. The resulting partial pressure is generally determined from Look-up tables having combined access parameters of Temperature and Solvent Flow Rate, which can be generated for any solvent. A part of a method of applying the present invention can involve developing a Look-up table for a particular solvent if one is not available.

It is noted that the terminology "liquid" and "solvent" are used in the foregoing primarily in regard to prior art, and the present invention, respectively.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for investigating changes in optical properties of a porous effective substrate that comprises a surface, related to at least one selection from the group consisting of:
   effective surface depth and refractive index;
   pore size;
   pore volume; and
   pore size distribution at atmospheric pressure;
said system enabling flowing of a gas that contains at least one solvent therein which is flowed over said substrate surface at a monitored temperature, over a sequence of different known solvent partial pressures, said system comprising:
   a) at least one source of a flow of at least one solvent and a solvent mass flow causing controller;
   b) a source of a flow of gas and a gas mass flow causing controller;
   c) an atomizing nozzle for receiving both a flow of at least one solvent and of a flow of gas, and expelling a mixture of said at least one solvent in said gas over said substrate at a sequence of solvent partial pressures;

d) an open chamber comprising said substrate that comprises a surface, and a temperature monitoring system sensor;

said system not comprising a partial pressure sensor feedback loop to control partial pressure values in said open chamber, but rather, partial pressure values in said open chamber are set entirely by direct control of solvent flow rate of said at least one solvent in view of a measured temperature;

such that in use said temperature monitoring sensor provides a measurement of temperature, and said atomizing nozzle receives both a flow of gas and at least one solvent from said gas and solvent mass flow causing controllers associated with said source of a flow of gas, and of said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures;

said partial pressure of said solvent being determined from said measured temperature and solvent flow rate.

2. A system as in claim 1, which further comprises an ellipsometer system comprising a polarization state generator oriented so as to direct a polarized beam of electromagnetic radiation at said surface of said substrate, and a polarization state detector oriented to detect said beam of electromagnetic radiation after it interacts with said surface of said substrate, and produce substrate surface characterizing data.

3. A system as in claim 1, in which the system is present in open atmosphere and wherein the static pressure in said open chamber is neither greater than or less than that of the open atmosphere.

4. A system as in claim 1, in which the system is present in a common ambient environment with other than atmosphere components in their common ratios, and wherein the static pressure in said open chamber is neither greater than or less than that of the common ambient atmosphere, which common ambient atmosphere is substantially equal to prevailing atmospheric pressure.

5. A system as in claim 1, in which a thin film is present on said substrate surface, and said thin film is investigated.

6. A system as in claim 1, in which the solvent is water.

7. A system as in claim 1, in which the solvent is other than water.

8. A method for investigating changes in optical properties of a substrate surface, comprising the steps of:
A) providing a system for investigating changes in optical properties of a porous effective substrate, that comprises a surface, related to at least one selection from the group consisting of:
effective surface depth and refractive index;
pore size;
pore volume; and
pore size distribution at atmospheric pressure;
said system enabling flowing of a gas that contains at least one solvent therein which is flowed over said substrate surface at a monitored temperature, over a sequence of different known solvent partial pressures, said system comprising:
a) at least one source of a flow of at least one solvent and a solvent mass flow causing controller;
b) a source of a flow of gas and a gas mass flow causing controller;

c) an atomizing nozzle for receiving both a flow of at least one solvent and of a flow of gas, and expelling a mixture of said at least one solvent in said gas over said substrate at a sequence of solvent partial pressures;

d) an open chamber comprising said substrate that comprises a surface, and a temperature monitoring sensor;

said system not comprising a partial pressure sensor feedback loop to control partial pressure values in said open chamber, but rather, partial pressure values in said open chamber are set entirely by direct control of solvent flow rate of said at least one solvent in view of a measured temperature;

such that in use said temperature monitoring sensor provides a measurement of temperature, and said atomizing nozzle receives both a flow of gas and at least one solvent from said gas and solvent mass flow causing controllers associated with said source of a flow of gas, and of said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures;

said partial pressure of said solvent being determined from said measured temperature and solvent flow rate;

said system further comprising:
e) providing an ellipsometer system comprising a polarization state generator oriented so as to direct a polarized beam of electromagnetic radiation at said surface of said substrate, and a polarization state detector oriented to detect said beam of electromagnetic radiation after it interacts with said surface of said substrate, and produce substrate surface characterizing data;

such that in use said atomizing nozzle receives both a flow of gas and at least one solvent from said source of a flow of gas and from said at least one source of a flow of at least one solvent, respectively, and in response expels a mixture of said at least one solvent in said gas, which mixture is caused to pass over said substrate surface in said open chamber in a manner such that said solvent transiently permeates said substrate surface long enough for data to be acquired therefrom, for each of a sequence of solvent partial pressures; and also in use said ellipsometer polarization state generator directs a polarized beam of electromagnetic radiation at said surface of said substrate, and a polarization state detector detects said beam of electromagnetic radiation after it interacts with said surface of said substrate, and produce substrate surface characterizing data;

B) causing said atomizing nozzle to receive both a flow of gas and at least one solvent from said source of a flow of gas and from said at least one source of a flow of at least one solvent via said gas and solvent mass flow causing controllers, respectively, and in response expel a mixture of said at least one solvent in said gas, so as to effect a sequence of solvent partial pressures, which mixture is caused to pass over said substrate surface in said open chamber in a manner such that said solvent transiently permeates said substrate surface long enough for data to be acquired therefrom by causing said ellipsometer polarization state generator to direct a polarized beam of electromagnetic radiation at said surface of said substrate, and said polarization state detector to detect said beam of electromagnetic radiation after it interacts with said surface of said substrate, and produce substrate effective surface characterizing data for at least some of said sequence of solvent partial pressures;

C) for a temperature provided by said temperature monitoring sensor of said open chamber, analyzing and/or displaying at least some of the effective substrate surface characterizing data.

9. A method as in claim 8, wherein at least two substrate surface associated parameters are evaluated as a function of solvent partial pressure of said at least one solvent at a known temperature, by analysis of produced substrate effective surface characterizing data, said at least two parameters being selected from the group consisting of:

substrate effective surface thickness;
substrate effective surface refractive index;
substrate surface pore size;
substrate surface pore volume; and
substrate surface pore size distribution.

10. A method as in claim 8, in which a thin film is present on said substrate surface, and said thin film is investigated.

11. A method as in claim 8, in which the solvent is water.

12. A method as in claim 8, in which the solvent is other than water.

13. A method as in claim 8, which further comprises developing a look-up table that comprises, for the solvent utilized, correlation between solvent flow rate and temperature, and partial pressure and using said table to determine specific partial pressures, given a solvent flow rate caused by said solvent mass flow causing controller, and said measured temperature.

* * * * *